(12) United States Patent
Tardivat et al.

(10) Patent No.: US 6,774,255 B1
(45) Date of Patent: Aug. 10, 2004

(54) POLYFUNCTIONAL ORGANOSILANE USABLE AS A COUPLING AGENT AND PROCESS FOR THE OBTAINMENT THEREOF

(75) Inventors: Jean-Claude Tardivat, Clermont-Ferrand (FR); Laure Belin, Riom (FR); Christiane Blanchard, Marsat (FR)

(73) Assignee: Michelin Recherche et Technique, S.A., Grange-Paccot (CH)

( * ) Notice: Subject to any disclaimer, the term of this patent is extended or adjusted under 35 U.S.C. 154(b) by 0 days.

(21) Appl. No.: 10/411,616

(22) Filed: Apr. 10, 2003

Related U.S. Application Data (63) Continuation of application No. PCT/EP01/11668, filed on Oct. 9, 2001.

Foreign Application Priority Data

Oct. 13, 2000 (FR) .............................. 00 13254

(51) Int. Cl.[7] .................................. C07F 7/08
(52) U.S. Cl. .................. 556/427; 556/466; 528/30
(58) Field of Search ................ 556/427, 466; 528/30

(56) References Cited

U.S. PATENT DOCUMENTS

| | | | |
|---|---|---|---|
| 3,842,111 A | | 10/1974 | Meyer-Simon |
| 3,997,581 A | * | 12/1976 | Pletka et al. ................ 556/408 |
| 4,201,698 A | * | 5/1980 | Itoh et al. .................... 524/83 |
| 4,390,648 A | * | 6/1983 | Stacy ......................... 523/216 |
| 5,314,752 A | * | 5/1994 | Bova et al. ............. 428/424.2 |
| 5,650,457 A | * | 7/1997 | Scholl et al. ................ 524/262 |
| 5,939,493 A | | 8/1999 | Hojo |
| 2003/0114601 A1 | * | 6/2003 | Cruse et al. ............ 525/332.6 |

FOREIGN PATENT DOCUMENTS

| | | |
|---|---|---|
| DE | 4435311 | 4/1996 |
| EP | 0 832 920 | 1/1998 |
| WO | WO 00/05301 | 2/2000 |

* cited by examiner

*Primary Examiner*—Jeffrey B. Roberston
(74) *Attorney, Agent, or Firm*—Felipe J. Farley; Christopher P. Crecente; Alan A. Csontos (57) ABSTRACT

A monohydroxysilane polysulfide of the formula:

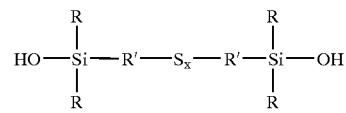

in which the radicals R, which may be identical or different, are hydrocarbon groups preferably comprising from 1 to 15 carbon atoms; the radicals R', which may be identical or different, are divalent linking groups preferably comprising from 1 to 18 carbon atoms; x is greater than or equal to 2. This hydroxysilane is in particular a bis-(propyidimethylsilanol) polysulfide. A process for obtaining such a hydroxysilane by alcoholysis and/or hydrolysis of a halogenated organosilane, followed by a sulfuration stage. Use of this hydroxysilane as a coupling agent.

30 Claims, 1 Drawing Sheet

POLYFUNCTIONAL ORGANOSILANE USABLE AS A COUPLING AGENT AND PROCESS FOR THE OBTAINMENT THEREOF

The present application is a continuation of International Application No. PCT/EP01/11668, filed 9 Oct. 2001, published in French with an English Abstract on 18 Apr. 2002 under PCT Article 21(2), which claims priority to French Patent Application No. FR 00/13254, filed 13 Oct. 2000.

FIELD OF INVENTION

The present invention relates to polyfunctional coupling agents usable in particular for coupling reinforcing inorganic fillers and diene elastomers in rubber compositions intended, for example, for the manufacture of tires.

BACKGROUND OF THE INVENTION

It is generally known that in order to obtain the optimum reinforcement properties imparted by a filler, the latter should be present in the elastomeric matrix in a final form which is both as finely divided as possible and distributed as homogeneously as possible. Now, such conditions may only be obtained insofar as the filler has a very good ability firstly to be incorporated into the matrix during mixing with the elastomer and to disagglomerate, and secondly to be dispersed homogeneously in this matrix.

It is fully known that carbon black has such abilities, which is generally not true of inorganic fillers. For reasons of mutual attraction, the inorganic filler particles have an irritating tendency to agglomerate together within the elastomeric matrix. These interactions have the harmful consequence of limiting the dispersion of the filler and hence the reinforcing properties to a substantially lower level than that which it would be theoretically possible to achieve if all the (inorganic filler/elastomer) bonds that could be created during the mixing operation were in fact obtained; these interactions furthermore tend to increase the consistency of the rubber compositions in the uncured state and therefore to make them more difficult to work ("processability") than in the presence of carbon black.

Since fuel economies and the need to protect the environment have become priorities, it has however, proved necessary to produce tires having reduced rolling resistance, without adversely affecting their wear resistance. This has been made possible in particular due to the discovery of new rubber compositions reinforced with specific inorganic fillers referred to as "reinforcing" fillers, which are capable of rivalling conventional tire-grade carbon black from the reinforcing point of view, and furthermore offering these compositions lower hysteresis, which is synonymous with lower rolling resistance for the tires comprising them.

Such rubber compositions, comprising reinforcing inorganic fillers of the siliceous or aluminous type, have for example been described in patents or patent applications EP-A-0501227 (or U.S. Pat. No. 5,227,425), EP-A-0735088 (or U.S. Pat. No. 5,852,099), EP-A-0810258 (or U.S. Pat. No. 5,900,449), EP-A-0881252, WO99/02590, WO99/02601, WO99/02602, WO99/28376, WO00/05300 and WO00/05301.

Mention will be made in particular of documents EP-A-0501227, EP-A-0735088 or EP-A-0881252, which disclose diene rubber compositions reinforced with precipitated silicas of high dispersibility, such compositions making it possible to manufacture treads having a significantly improved rolling resistance, without adversely affecting the other properties, in particular those of grip, endurance and wear resistance. Such compositions having such a compromise of contradictory properties are also described in applications EP-A-0810258 and WO99/28376, with specific aluminous fillers (aluminas or aluminium (oxide-)hydroxides) of high dispersibility as reinforcing inorganic fillers, or alternatively in applications WO00/73372 and WO00/73373, which describe specific titanium oxides of the reinforcing type.

Although the use of these specific, highly dispersible inorganic fillers as reinforcing fillers, whether or not as the majority component, has reduced the difficulties of processing the rubber compositions containing them, such compositions are still more difficult to process than are rubber compositions filled conventionally with carbon black.

In particular, it is necessary to use a coupling agent, also known as a bonding agent, the function of which is to provide the connection between the surface of the inorganic filler particles and the elastomer, while facilitating the dispersion of this inorganic filler within the elastomeric matrix.

It will be recalled that (inorganic filler/elastomer) "coupling agent" should, in known manner, be taken to mean an agent capable of establishing a sufficient chemical and/or physical connection between the inorganic filler and the diene elastomer; such a coupling agent, which is at least bifunctional, has, for example, the simplified general formula "Y—W—X", in which:

Y represents a functional group ("Y" function) which is capable of bonding physically and/or chemically with the inorganic filler, it being possible to establish such a bond, for example, between a silicon atom of the coupling agent and the hydroxyl (OH) surface groups of the inorganic filler (for example, surface silanols in the case of silica);

X represents a functional group ("X" function) which is capable of bonding physically and/or chemically with the diene elastomer, for example by means of a sulfur atom;

W represents a divalent group making it possible to link Y and X.

The coupling agents must in particular not be confused with simple agents for covering the inorganic filler which, in known manner, may comprise the Y function which is active with respect to the inorganic filler but are devoid of the X function which is active with respect to the diene elastomer.

Coupling agents, in particular silica/diene elastomer coupling agents, have been described in numerous documents, the best known being bifunctional organosilanes bearing at least one alkoxyl function as the Y function, and, as the X function, at least one function capable of reacting with diene elastomer, such as for example a sulfur function (i.e. comprising sulfur).

Thus it was proposed in patent applications FR-A-2094859 or GB-A-1310379 to use a mercaptoalkoxysilane coupling agent for the manufacture of treads for tires. It was quickly shown, and is today well known, that mercaptoalkoxysilanes are capable of giving excellent silica/elastomer coupling properties, but that these coupling agents cannot be used industrially because of the high reactivity of the thiol-SH type sulfurised functions (X functions), which very rapidly results in premature vulcanization during the preparation of the rubber composition in an internal mixer, this also being known as "scorching", in very high viscosities in the uncured state and, finally, in rubber compositions which are virtually impossible to work and process industrially. Mention may be made, for example, of documents FR-A-2206330, U.S. Pat. No. 3,873,489, U.S. Pat. No. 4,002,594 to illustrate this problem.

To overcome this drawback, it has been proposed to replace these mercaptoalkoxysilanes by alkoxysilane polysulfides, in particular bisalkoxysilylpropyl) polysulfides such as described in numerous documents (see for example FR-A-2149339, FR-A-2206330, U.S. Pat. No. 3,842,111, U.S. Pat. No. 3,873,489, U.S. Pat. No. 3,997,581, EP-A-680997 or U.S. Pat. No. 5,650,457, EP-A-791622 or U.S. Pat. No. 5733963, DE-A-19951281 or EP-A-1043357, WO00/53671). Among these polysulfides, bis-3-triethoxysilylpropyl tetrasulfide (abbreviated to TESPT) and bis-3-triethoxysilylpropyl disulfide (abbreviated to TESPD) must in particular be mentioned.

These alkoxysilane polysulfides, in particular TESPT, are generally considered to be the products which achieve, for vulcanized rubber compositions comprising a reinforcing inorganic filler, in particular silica, the best compromise in terms of resistance to scorching, ease of processing and reinforcing action. Today, they are in this respect the most widely used coupling agents in rubber compositions for tires, even if they are relatively costly and, furthermore, must most frequently be used in a relatively large quantity.

The alkoxysilane polysulfides do, however, have the disadvantage of substantially retarding the vulcanization kinetics of the rubber compositions containing them in comparison with the kinetics of conventional compositions reinforced with carbon black. The resultant longer duration of curing may impair industrial processing of these rubber compositions reinforced with inorganic fillers and of the rubber articles containing them.

BRIEF SUMMARY OF THE INVENTION

The Applicants have now discovered in the course of their research certain novel and specific organosilanes which, unexpectedly, provide a remedy to this drawback relating to curing kinetics, furthermore without impairing coupling and thus reinforcement, and so provide for elastomer compositions an improved compromise of properties in comparison with that hitherto achieved with polysulfurised alkoxysilanes, in particular with TESPT.

These specific alkoxysilanes furthermore do not have the aforementioned problems of premature scorching and of processing which are due to excessive viscosity of the rubber compositions in the uncured state, which disadvantages are inherent in mercaptoalkoxysilanes.

A first subject of the invention is accordingly a monohydroxysilane polysulfide of the formula (I):

in which the radicals R, which may be identical or different, are hydrocarbon groups; the radicals R', which may be identical or different, are divalent linking groups; x is greater than or equal to 2.

As far as the Applicants are aware, such a polysulfurised monohydroxysilane has never hitherto been synthesised, in particular with the purpose of use as a coupling agent due to the strong prejudices regarding the recognised instability of organosilanes bearing hydroxyl functions. It should be recalled here that this instability is due to the strong propensity of hydroxysilyl groups (≡Si—OH), especially in the presence of strong acids (which are moreover generated during synthesis of organoxysilanes from halogenated silanes), to condense with themselves to form ≡Si—O—Si≡ linkages, in other words siloxane linkages; this mechanism is moreover exploited in the synthesis of polysiloxanes (see for example for the following references: "*The Chemistry of organic silicon compounds*", S. Patal and Z. Rappoport, John Wiley & Sons, 1989, Part 1, 722–725; "*Siloxane polymers*", S. J. Clarson and J. A. Semlyen, Ellis Horwood Pretice-Hall, Elgelwood Cliffs N.J., 1993, 577–578; 597).

A further subject of the invention is a process for the obtainment of a monohydroxysilane according to the invention comprising the following steps (R and R' having the above meanings):

the starting compound is a halogenated organosilane (hereafter product A) of the formula (A) (Hal= halogen):

said organosilane is optionally subjected to alcoholysis under the action of an alcohol (R"—OH) in the presence of an organic base intended to scavenge the resultant acid halide, in order to obtain a monoalkoxysilane of the formula (B) (hereafter product B):

hydrolysis by the action of a hydroxyl donor is performed in an inert organic solvent:
either on the product (A) in the presence, in this case, of an organic base to scavenge the resultant acid halide, the hydroxyl donor being water;
or, if applicable, on the product (B), the hydroxyl donor being a inorganic base and the organic solvent a polar solvent, in order to obtain a monohydroxysilane (product C) of the formula (C):

finally, a sulfuration stage is performed on the product C by the action of a polysulfide to give rise to the intended product of the formula (I).

The subject of the invention is also the use of a monohydroxysilane according to the invention as coupling agent, in particular as (inorganic filler/diene elastomer) coupling agent in a rubber composition.

The invention and its advantages will be readily understood in the light of the description and examples of embodiment which follow, together with the figures relating to those examples, which show.

I. Measurements and Tests Used

The rubber compositions in which the organosilane coupling agents are tested are characterised before and after curing, as indicated below.

I-1. Mooney Plasticity

An oscillating consistometer such as described in French Standard NF T 43-005 (1991) is used. Mooney plasticity is measured in accordance with the following principle: the raw composition (i.e. before curing) is moulded in a cylindrical enclosure heated to 100° C. After one minute's preheating, the rotor turns within the test specimen at 2 rpm, and the torque used for maintaining this movement is measured after four minutes' rotation. Mooney plasticity (ML 1+4) is expressed in "Mooney units" (MU, with 1 MU=0.83 N.m).

I-2. Scorching Time

The measurements are made at 130° C., in accordance with French Standard NF T 43-005 (1991). The change in the consistometric index as a function of time makes it possible to determine the scorching time for the rubber compositions, assessed in accordance with the above standard by the parameter T5 (case of a large rotor), expressed in minutes, and defined as being the time necessary to obtain an increase in the consistometric index (expressed in MU) of 5 units above the minimum value measured for this index.

I-3. Tensile Tests

These tests make it possible to determine elasticity stresses and breaking properties. Unless indicated otherwise, they are performed in accordance with French Standard NF T 46-002 of September 1988. The nominal secant moduli (or apparent stresses, in MPa) at 10% elongation (M10), 100% elongation (M100) and 300% elongation (M300) are measured in a second elongation (i.e. after a cycle of accommodation to the amount of extension provided for the measurement itself). Breaking stresses (in MPa) and elongations at break (in %) are also measured. All these tensile measurements are performed under normal conditions of temperature and relative humidity in accordance with French Standard NF T 40-101 (December 1979).

Processing the tensile data recorded also makes it possible to plot the curve of modulus as a function of elongation (see attached FIG. 2), the modulus used here being the true secant modulus measured in a first elongation, calculated on the basis of the true cross-section of the test specimen and not on the basis of the initial cross-section as previously for the nominal moduli.

I-4. Dynamic Properties

Dynamic properties are measured on a viscoanalyser (Metravib VA4000), in accordance with ASTM Standard D5992-96. The response of a sample of vulcanized composition (cylindrical test specimen of a thickness of 4 mm and a cross-section of 400 mm$^2$), subjected to an alternating single sinusoidal shearing stress, at a frequency of 10 Hz, under normal temperature conditions (23° C.) in accordance with Standard ASTM D 1349-99, is recorded. Scanning is performed at an amplitude of deformation of 0.1 to 50% (outward cycle), then of 50% to 1% (return cycle); on the return cycle, the maximum observed value of the loss factor tan($\delta$) is recorded, the value being denoted tan($\delta$)$_{max}$.

I-5. Rheometry

The measurements are performed at 150° C. using an oscillating chamber rheometer in accordance with Standard DIN 53529, part 3 (June 1983). The change in rheometric torque over time describes the course of stiffening of the composition as a result of the vulcanization reaction (see FIG. 1 attached). The measurements are processed in accordance with Standard DIN 53529, part 2 (March 1983): minimum and maximum torque values, measured in deciNewton.meter (dN.m) are respectively denoted $C_{min}$ and $C_{max}$; $t_i$ is the induction time, i.e. the time required for the vulcanization reaction to begin; $t_\alpha$ (for example $t_{99}$) is the time necessary to achieve conversion of $\alpha\%$, i.e. $\alpha\%$ (for example 99%) of the difference between the minimum and maximum torque values. The difference, denoted $\Delta$torque (in dN.m), between minimum and maximum torque values is also measured, as is the conversion rate constant K (in min$^{-1}$), which allows an assessment of vulcanization kinetics to be made.

II. Conditions of Carrying Out the Invention

II-1. Polysulfurised Hydroxysilane of the Invention

The first subject of the invention is a monohydroxysilane polysulfide (where $x \geq 2$, i.e. including disulfide) of the above-mentioned formula (I), in which the radicals R, which may be identical or different, are hydrocarbon groups, the radicals R', which may be identical or different, are divalent linking groups, and x is greater than or equal to 2.

Such an organosilane fulfils the definition of a coupling agent, in that each molecule comprises:
- on one hand at least one functional group (polysulfide function $S_x$ as "X" function) capable of forming a stable bond with a polymer such as a diene elastomer;
- on the other hand a hydroxyl group (OH) on each silicon atom, which function is known as a hydroxysilyl function ($\equiv$Si—OH), as "Y" function, which allows the function to graft onto various (for example metallic or mineral) substrates, such as the surface of a reinforcing inorganic filler.

The radicals R, which may be straight-chain or branched, preferably comprise from 1 to 15 carbon atoms; these are more preferably selected from among alkyls, cycloalkyls or aryls, in particular from among $C_1$–$C_6$ alkyls, $C_5$–$C_8$ cycloalkyls and the phenyl radical. Among these radicals, those selected from the group consisting of methyl, ethyl, n-propyl, isopropyl, n-butyl, sec.-butyl, tert.-butyl, n-pentyl, neopentyl, n-hexyl, 2-ethylhexyl, n-octyl, isooctyl, cyclopentyl, cyclohexyl, 2-methylcyclohexyl, phenyl, toluyl, benzyl may in particular be mentioned by way of example.

More preferably still, they are $C_1$–$C_3$ alkyls, (namely methyl, ethyl, n-propyl, isopropyl), very particularly selected from among methyl or ethyl.

The radicals R', whether substituted or unsubstituted, are preferably saturated or unsaturated hydrocarbon radicals, comprising from 1 to 18 carbon atoms, the hydrocarbon chains of these radicals R' possibly being interrupted by at least one heteroatom such as O, S or N. In particular $C_1$–$C_{18}$ alkylene groups or $C_6$–$C_{12}$ arylene groups, more particularly $C_1$–$C_{10}$ alkylenes, notably $C_1$–$C_4$ alkylenes, in particular those selected from among methylene, ethylene and propylene, are suitable.

In other words, the polysulfurised monohydroxysilane of the invention is more preferably a bis-(monohydroxy-($C_1$–$C_{18}$)-alkyl-silyl($C_1$–$C_{15}$)alkyl) polysulfide (symmetrical or asymmetrical with regard to the nature of the radicals R or R') of the general formula (I) above, in particular a bis-(monohydroxy-($C_1$–$C_3$)-alkyl-silyl(methyl, ethyl or propyl) polysulfide.

Among the hydroxysilanes of the formula (I), those which are particularly preferred are those in which the radicals R are $C_1$–$C_3$ alkyls and the radicals R' are $C_1$–$C_4$ alkylenes, with x being greater than or equal to 2.

Among these latter, bis-[($C_1$–$C_4$)-alkyldimethylsilanol] polysulfides, where R=Me (methyl) of the formula (II) below may in particular be mentioned:

in which $x \geq 2$ and the radicals R' are $C_1$–$C_4$ alkylene, in particular methylene, ethylene or propylene, more particularly propylene.

By way of example, a bis-(propyldimethylsilanol) polysulfide of the specific formula (III) below may be mentioned:

In these formulae (I) to (III), the number x of sulfur atoms may vary widely, for example from 2 to 9, depending upon the particular conditions under which the monohydroxysilane was synthesised; however, the values of x are preferably selected within the range from 2 (disulfides) to 6 (hexasulfides) and including the corresponding trisulfides (x=3), tetrasulfides (x=4) and pentasulfides (x=5). More preferably still, x is selected from within the range from 2 to 4.

The above polysulfurised monohydroxysilanes may be prepared in accordance with a novel synthesis process, which is another subject of the present invention.

II-2. Synthesis Process

The process of the invention for preparing a monohydroxysilane of the formula (I) above comprises the following steps:

the starting compound is a halogenated organosilane (hereafter product A) of the formula (A) (Hal= halogen):

said organosilane is optionally subjected to alcoholysis under the action of an alcohol (R"—OH) in the presence of an organic base intended to scavenge the resultant acid halide, in order to obtain a monoalkoxysilane of the formula (B) (hereafter product B):

hydrolysis by the action of a hydroxyl donor is performed in an inert organic solvent:
either on the product (A) in the presence, in this case, of an organic base to scavenge the resultant acid halide, the hydroxyl donor being water;
or, if applicable, on the product (B), the hydroxyl donor being a inorganic base and the organic solvent a polar solvent, in order to obtain a monohydroxysilane (product C) of the formula (C):

finally, a sulfuration stage is performed on the product C by the action of a polysulfide to give rise to the intended product of the formula (I).

Certain stages (alcoholysis, sulfuration) of this process according to the invention have already been applied, at least in general terms, to the synthesis of sulfurised alkoxysilanes, such as mercaptoalkoxysilanes or polysulfide alkoxysilanes (see in particular FR-A-2149339 or U.S. Pat. No. 4,076,550, FR-A-2206330, EP-A-0694552 or U.S. Pat. No. 5,405,985). However, as far as the Applicants are aware, the above stages have never hitherto been described in combination in order to obtain polysulfurised monohydroxysilanes.

The halogens (Hal) of the starting silane (product A) may be identical or different and preferably be selected from among bromine and chlorine; chlorine is more preferably used. Generally, the starting halosilanes (products A) and their intermediate derivatives (products B or C) are liquids; they may thus be used as they are or alternatively diluted in an appropriate solvent during the implementation of the various stages of the process of the invention.

The first, optional, alcoholysis stage thus consists in replacing the halogen (Hal) borne by the silicon atom of the product A with the alkoxyl group (OR") of an alcohol in the presence of an organic base intended to scavenge the acid halide liberated during the course of the reaction. The hydrocarbon radical R" of the alcohol (R"—OH) preferably comprises from 1 to 8 carbon atoms; it is more preferably selected from among $C_1$–$C_6$ alkyls, more preferably still from among $C_1$–$C_3$ alkyls, in particular methyl or ethyl. An amine, preferably a tertiary amine such as triethylamine may be used as the organic base intended to scavenge the acid halide which is formed. In order to improve scavenging of the acid halide, alcoholysis is performed at a temperature which is preferably less than 15° C., more preferably less than 10° C.

The hydrolysis stage may also be performed directly on the starting halogenated silane (product A), by the action of water in an inert inorganic solvent, for example an ether, and in the presence of an organic base intended, as above, to scavenge the acid halide which is formed.

The starting halogenated silane is, however, preferably alcoholysed before being hydrolysed. This hydrolysis of the product B is carried out in a polar organic solvent, preferably an alcohol, by the action of an inorganic base in an aqueous solution; the inorganic base is preferably an alkali metal or alkaline-earth metal hydroxide, in particular sodium hydroxide (NaOH). The base is preferably used in slight excess, this excess being neutralised at the end of the reaction by a weak acid such as potassium dihydrogenphosphate. The polar organic solvent is preferably a $C_1$–$C_6$ alcohol, more preferably a $C_1$–$C_3$ alcohol, more particularly methanol.

The final sulfuration stage may be performed using an ammonium or metal polysulfide ($x \geq 2$), of the formula $M_2S_x$ or $M'S_x$ (M=alkali metal or $NR_4$; M'=Zn or alkaline-earth metal); examples of such compounds are the polysulfides of Na, K, Cs, Rb, Ca, Mg, Zn and $NH_4$, x preferably being within the range from 2 to 6, more preferably from 2 to 4. A sodium polysulfide $Na_2S_x$, in particular $Na_2S_2$, $Na_2S_3$, $Na_2S_4$, $Na_2S_5$, $Na_2S_6$, this polysulfide preferably being obtained by the action of sulfur ($S_8$) on $Na_2S$, is preferably used. In known manner, the polysulfides are prepared in a solvent, which may be organic or inorganic, such as for example water, alcohols, ketones or ethers, solvents in which the reaction partners are partially or entirely soluble.

However, in order to eliminate any risk of forming secondary products of the alkoxysilane polysulfide type, due to a parasitic alcoholysis reaction of the silanol functions of product C, it is preferred to perform the sulfuration stage in the absence of any alcohol; in this case, the reaction is preferably performed in aqueous phase, more preferably in a biphasic water/organic solvent medium (for example toluene, xylene, benzene, heptane or equivalents), as described in the aforementioned documents EP-A-0694552 or U.S. Pat. No. 5,405,985 relating to the synthesis of polysulfurised alkoxysilanes. The reaction is then performed in known manner in the presence of a phase-transfer catalyst and a salt of the formula M"Hal or M"$SO_4$ (M" selected from among Li, Na, K; Hal selected from among F, Cl and Br). The salt used is preferably selected from among NaCl, NaBr, $Na_2SO_4$; NaCl is more preferably used. The quantity of salt may vary, for example, from 10% by weight of the aqueous solution up to complete saturation of the solution. The phase-transfer catalyst is, for example, tetrabutylammonium bromide (TBAB).

The sulfuration stage is preferably performed under an inert gas such as argon. The temperature of the reaction medium is not critical, it being, for example, possible to work at ambient temperature; it is, however, preferred work at elevated temperature to increase the speed of reaction, for example between 60° C. and 100° C., even up to the boiling point of the solvent. The molar ratio between hydroxysilane (product C) and the (ammonium or metal) polysulfide is preferably adjusted so as to achieve a slight excess of polysulfide relative to the stoichiometric quantity.

If sulfuration is performed in the organic phase, product C is itself preferably pre-diluted in the inert organic solvent such as an alcohol, a ketone or an ether. Once the reaction is complete, the salt (metal halide) which has formed is filtered out and the organic solvent is removed from the filtrate by vacuum distillation. When sulfuration is performed in the aqueous phase or biphasic medium (water/organic solvent), if applicable, the organic phase containing the product D is isolated and the residual solvent is distilled under a vacuum.

The polysulfurised monohydroxysilanes synthesised in accordance with the process described above are in fact mixtures of polysulfides (for example of x=2 to x=9), which consequently have an average value of x which is other than an integer. The intended average value for x is preferably between 2 and 6, more preferably within a range from 2 to 4.

II-3. Use as Coupling Agent

As indicated above, by virtue of its double functionality, the compound of the invention has an advantageous industrial application as a coupling agent intended, for example, to create a link or bond between a reactive polymeric matrix (in particular a rubber matrix) and any material having a hydroxylated surface, in particular a mineral (for example a glass fibre) or metallic material (for example a carbon steel or stainless steel wire).

Without this being limitative, the compound may in particular be used for coupling white fillers or reinforcing inorganic fillers and diene elastomers, for example in rubber compositions intended for tire manufacture. "Reinforcing inorganic filler" is understood in known manner to mean an inorganic or mineral filler, whatever its colour and its origin (natural or synthetic), also referred to as "white" filler or sometimes "clear" filler in contrast to carbon black, this inorganic filler being capable, on its own, without any other means than an intermediate coupling agent, of reinforcing a rubber composition intended for the manufacture of tires, in other words which is capable of replacing a conventional tire-grade carbon black filler in its reinforcement function.

For such use, the diene elastomer is then preferably selected from the group of highly unsaturated diene elastomers consisting of polybutadienes (BR), synthetic polyisoprenes (IR), natural rubber (NR), butadiene-styrene copolymers (SBR), butadiene-isoprene copolymers (BIR), butadiene-acrylonitrile copolymers (NBR), isoprene-styrene copolymers (SIR), butadiene-styrene-isoprene copolymers (SBIR) and mixtures of these elastomers.

When the monohydroxysilane inorganic filler is intended for (inorganic filler/diene elastomer) coupling in a rubber composition constituting, for example, all or part of a passenger-car tire tread, the diene elastomer is then preferably an SBR or a blend (mixture) of SBR and another diene elastomer such as BR, NR or IR. When an SBR elastomer is used, it is in particular an SBR having a styrene content of between 20% and 30% by weight, a content of vinyl bonds of the butadiene moiety of between 15% and 65%, a content of trans-1,4 bonds of between 15% and 75%, and a glass transition temperature ("Tg", measured in accordance with ASTM Standard D3418-82) of between −20° C. and −55° C., this SBR copolymer, which is preferably prepared in solution (SSBR), possibly being used in a mixture with a polybutadiene (BR) having preferably more than 90% cis-1,4 bonds.

When the tread is intended for a utility vehicle tire, such as a heavy vehicle tire, the diene elastomer is then preferably an isoprene elastomer, i.e. a diene elastomer selected from among the group consisting of natural rubber (NR), synthetic polyisoprenes (IR), the various isoprene copolymers and mixtures of these elastomers; in this case, the rubber more preferably comprises natural rubber or a synthetic polyisoprene of the cis-1,4 type having a content (mol %) of cis-1,4 bonds of greater than 90%, still more preferably of greater than 98%.

The polysulfurised monohydroxysilanes of the invention have alone proved sufficiently effective to couple a diene elastomer and a reinforcing inorganic filler such as silica, used in a preferred amount of greater than 1 phr (parts by weight per hundred parts of elastomer), more prtferably of between 2 and 20 phr. They may advantageously constitute the sole coupling agent present in the rubber compositions reinforced with inorganic filler and intended for tire manufacture.

Reinforcing inorganic fillers which may be mentioned are mineral fillers of the siliceous type, in particular silica ($SiO_2$), or aluminous type, in particular alumina ($Al_2O_3$) or aluminium (oxide-)hydroxides, or also reinforcing titanium oxides, as described in the above-mentioned patents or patent applications.

The hydroxysilanes of the invention could also be used in a form already grafted onto the reinforcing inorganic filler (via their hydroxysilyl function), it then being possible to bond the inorganic filler "precoupled" in this manner to the diene elastomer by means of the free polysulfide function $S_x$.

III. Examples of Embodiment of the Invention

In the following examples of embodiment, the invention is implemented with a bis-(propyidimethylsilanol) polysulfide of the specific formula (III):

III-1. Synthesis of the Polysulfurised Monohydroxysilane

This test first of all describes the synthesis of the compound of the formula (III) above (hereafter denoted product D) using a process according to the invention performed in two or three stages starting from chloropropyldimethylchlorosilane (hereafter denoted product A), via chloropropyldimethylethoxysilane (hereafter denoted product B; optional step) and chloropropyldimethylsilanol (hereafter denoted product C).

The synthesis scheme used is as follows:

a) Preparation of Chloropropyldimethylethoxysilane (Product B)

The first stage comprises an alcoholysis which permits the replacement of the chlorine borne by the silicon atom of product A by an ethoxyl group of the ethanol, this reaction being performed in the presence of triethylamine intended to scavenge the hydrochloric acid liberated during the reaction.

950 ml of ethanol (Normapur grade) then 288 mL of triethylamine (2.07 mol or 209 g) are introduced under a stream of argon using a syringe into a 2 L (litre) three-necked flask (which has previously been dried in an oven for 24 h), fitted with a condenser and equipped with a magnetic stirrer. The mixture is then cooled to a temperature of approx. 5° C. before addition of product A (237.7 g or 1.38 mol, product of ABCR sold under the reference SIC2336.0) is begun using a peristaltic pump; the liberated hydrochloric acid is immediately scavenged by the triethylamine to form triethylamine chlorohydrate.

Once addition is complete (after approx. 8 h), the ice bath is removed while stirring is continued at ambient temperature overnight under a stream of argon. After eight hours, GPC (gas phase chromatography) analysis demonstrates the disappearance of the peak corresponding to starting product A and the formation of chloropropyldimethylethoxysilane (product B). The reaction medium is then filtered through an Alhin tube in order to separate the product B dissolved in ethanol from the triethylamine chlorohydrate.

The filtrate containing the product B is concentrated then vacuum distilled (2 mm Hg; oil bath temperature 70° C.; overhead temperature 45° C.), in order to remove the excess free triethylamine and isolate product B in the pure state.

In this manner, 160 g of a colourless liquid are collected, analysis of which by NMR and mass spectrometry reveals that it is indeed the intended product B of the following formula:

b) Preparation of Chloropropyldimethylsilanol (Product C)

This second stage consists of hydrolysing the preceding ethoxysilane (in solution in methanol) to obtain the hydroxysilane. This reaction is carried out by the action of an aqueous solution of NaOH; after the reaction, the excess base introduced initially is neutralised with potassium dihydrogenphosphate.

2.62 g of sodium hydroxide (65 mmol or 2.4 equivalents relative to product B) are introduced into a 100 mL three-necked flask fitted with a condenser and equipped with a magnetic stirrer and are dissolved in 15 mL of demineralised water. Once dissolution is complete and when the temperature of the solution has returned to ambient temperature, 20 mL of methanol are added followed by, using a dropping funnel, the previously prepared product B (5 g or 27.7 mmol) diluted in 35 mL of methanol. The reaction medium is then stirred for 90 minutes, then poured into an aqueous solution of potassium dihydrogenphosphate (16 g of $KH_2PO_4$ in 200 mL of water). The resultant solution, which has a pH of 7, is stirred for a few minutes before being combined with 200 mL of ether intended to extract the product C which has formed. The biphasic medium is then stirred for approx. 30 to 45 min, then placed in a separating funnel. The isolated organic phase is washed once with water then dried over $MgSO_4$ before being filtered and then concentrated under a vacuum.

The GPC chromatogram of the crude reaction product collected in this manner exhibits three peaks which may respectively be assigned to (i) chloropropyldimethylethoxysilane, probably arising from the reaction of methanol on product B (of the order of 2% of units according to $^1$H NMR), (ii) the intended product C, in a large majority (85% of units according to $^1$H NMR), together with (iii) bis(chloropropyl)tetramethyidisiloxane (present in an amount of 13% of units).

The product C can be isolated by vacuum distillation, performed in a bulb tube oven (Kugelrohr). During this distillation, the selected temperature of the oven is preferably below 45° C. in order to minimise any risk of the product C condensing to yield the corresponding disiloxane. Thus, once the chloropropyldimethylmethoxysilane has been removed by applying a vacuum of 1.3 mbar and a temperature of 35° C., product C is isolated under a vacuum of 1 mbar by raising the temperature to 40° C.; due to its higher boiling point, the bis(chloropropyl)tetramethyidisiloxane remains in the distillation flask.

In this manner, 2.48 g of a pure colourless liquid are isolated, analysis of which by NMR and mass spectrometry reveals that product C of the following formula has been obtained:

As has been explained previously, product C above may also be prepared directly by hydrolysing the starting product A in an inert organic solvent (ether), in the presence of water as hydroxyl donor and of triethylamine intended to scavenge the hydrochloric acid which is liberated. An excess of water is preferably introduced so as to promote the desired reaction and to avoid the condensation reaction of the resultant silanol on the added chlorosilane. Using a slight excess of triethylamine ensures that all the hydrochloric acid is scavenged, any residual triethylamine being distilled off once the reaction is complete.

More specifically, the following method is used: 9.78 mL of triethylamine (70.1 mmol, or 1.5 equivalents relative to product A), 3.36 g of water (187 mmol, or 4 equivalents relative to product A), then 150 mL of ether are introduced into a 500 mL three-necked flask fitted with a condenser and equipped with a magnetic stirrer. This solution is cooled with an ice bath (temperature <10° C.) before slowly adding a solution of product A (8.0 g or 46.7 mmol in 80 mL of ether). A white precipitate, corresponding to triethylamine chlorohydrate, appears immediately. Once addition of product A is complete, the reaction medium is stirred for 30 min, while maintaining a temperature of less than 10° C. The precipitate which has formed is then filtered out and the collected filtrate is dried over magnesium sulfate, filtered and then concentrated under a vacuum. The residual triethylamine is removed by distillation. In this manner, 6.1 g of a brilliant yellow liquid are collected which, according to analysis by NMR and mass spectrometry, corresponds to the intended product C (product purity greater than 95%).

c) Preparation of Polysulfurised Hydroxysilane (Product D)

In this final stage, the sodium polysulfide, created by inserting sodium into sodium sulfide $Na_2S$ in an aqueous medium, replaces the chlorine atom with two molecules of product C in solution in toluene. The reaction is performed in the presence of a phase-transfer catalyst (TBAB) and sodium chloride, NaCl.

3.50 g (or 14.5 mmol) of $Na_2S.9H_2O$ together with 1.40 g (or 43.7 mmol) of sulfur, which are dissolved in 40 mL of an aqueous NaCl solution (5.0 g or 85.8 mmol) and 8 mL of toluene are introduced into a 250 mL three-necked flask fitted with a condenser and equipped with a magnetic stirrer. This mixture is heated to 85° C.; as the temperature rises, the reaction medium is observed to change in colour from yellow to a deep red.

Once the setpoint temperature has been reached, 0.25 g of TBAB (or 0.77 mmol) is added in a single portion, then dropwise addition of product C (4.60 g or 28.6 mmol) dissolved in 30 mL of toluene is begun. During addition, the toluene phase is of a bright red colour progressively turning towards orange, while the initially bright red aqueous phase becomes paler, finally becoming colourless and clear, once addition is complete. The reaction is thus continued for 75 min at the temperature of 85° C., then the reaction medium is cooled under argon.

The reaction medium is then transferred into a separating funnel so as to isolate the toluene phase, which is dried over magnesium sulfate after being washed with water. The organic solution is then filtered and reextracted with ether before being distilled in a bulb tube oven (40° C.) before recovering the residual chloropropyldimethylsilanol (product C).

Finally, 3.82 g of a viscous red-orange liquid are recovered, analysis of which by NMR and mass spectrometry confirm that it comprises (in mol %):

approx. 95% of bis-(propyidimethylsilanol) polysulfide of the formula (III):

approx. 5% of cyclic siloxane compound of the formula (IV) below:

The product D synthesised in this manner in fact consists of a distribution of polysulfides ranging from the disulfide (x=2) to hexasulfide (x=6), centred on an average value of x=3.7. The disulfide $S_2$ content, determined by NMR, is equal to approx. 18% of the polysulfide units.

This product thus consists, as is the case in particular for alkoxysilane polysulfides such as TESPT, of a distribution of polysulfides having an average value of x close to 4. It will be understood that modified synthesis conditions could permit the production of other polysulfide distributions having variable average values of x, but preferably between 2 and 6, more preferably in a range from 2 to 4.

III-2. Use as Coupling Agent

The object of this test is to demonstrate the improved performance of the hydroxysilane of the invention as a coupling agent in a rubber tire composition, compared with a conventional coupling agent (alkoxysilane polysulfide, TESPT), which is the reference substance in this domain.

For this, therefore, two rubber compositions based on SBR and BR elastomers and reinforced with silica, denoted C-1 and C-2, are prepared, these compositions being intended for treads for passenger-car tires. These compositions are identical with the exception of the coupling agent used:

composition C-1: TESPT;
composition C-2: product D synthesised above;

These compositions are prepared in known manner as follows: the diene elastomer (or the mixture of diene elastomers, if applicable), the reinforcing filler, the coupling agent, then the various other ingredients, with the exception of the vulcanization system, are introduced into an internal mixer filled to 70%, the initial tank temperature of which is approximately 60° C. Initial thermomechanical working (non-productive phase) is then performed in one or two stages (total duration of kneading equal to about 7 minutes), until a maximum "dropping" temperature of about 165° C. is reached. The mixture thus obtained is recovered, cooled, then the vulcanization system (sulfur and sulfenamide accelerator) is added in an external mixer (homo-finisher) at 30° C. by mixing everything ("productive" phase) for 3 to 4 minutes. The compositions are then calendered in the form of sheets (thickness of 2 to 3 mm) or of thin films of rubber in order to measure their physical or mechanical properties, or extruded to form profiled elements which can be used directly, after cutting out and/or assembly to the dimensions desired, for example as semi-finished products for tires, in particular as treads for passenger-car tires.

It will be recalled that TEPST (composition C-1) is bis(1-triethoxysilylpropyl) tetrasulfide, of the formula $[(C_3H_2O)_5Si(CH_3)_2S_2]_2$; it is sold, for example, by Degussa under the name "Si69" (or "X50S" when it is supported to 50% by weight on carbon black), or alternatively by Witco under the name "Silquest A1289" (in both cases, a commercial mixture of polysulfides $S_x$ having an average value of x which is close to 4).

The full formula of TESPT is (Et=ethyl):

It will be noted that the above structure is very close to that of the monohydroxysilane of the invention tested here (formula III), this latter differing only in the presence of a hydroxyl group and two methyls instead of three conventional alkoxyl groups.

Tables 1 and 2 show the formulation of the two compositions (Table 1—amounts of the different products expressed in phr), and their properties before and after curing (approx. 30 min at 150° C.); the vulcanization system consists of sulfur and sulfenamide accelerator. The two compositions tested additionally comprise (not stated in Table 1) a small proportion of carbon black N330 (6 phr) used as a black pigment and anti-UV agent.

BRIEF DESCRIPTION OF THE DRAWINGS

Figure 1:
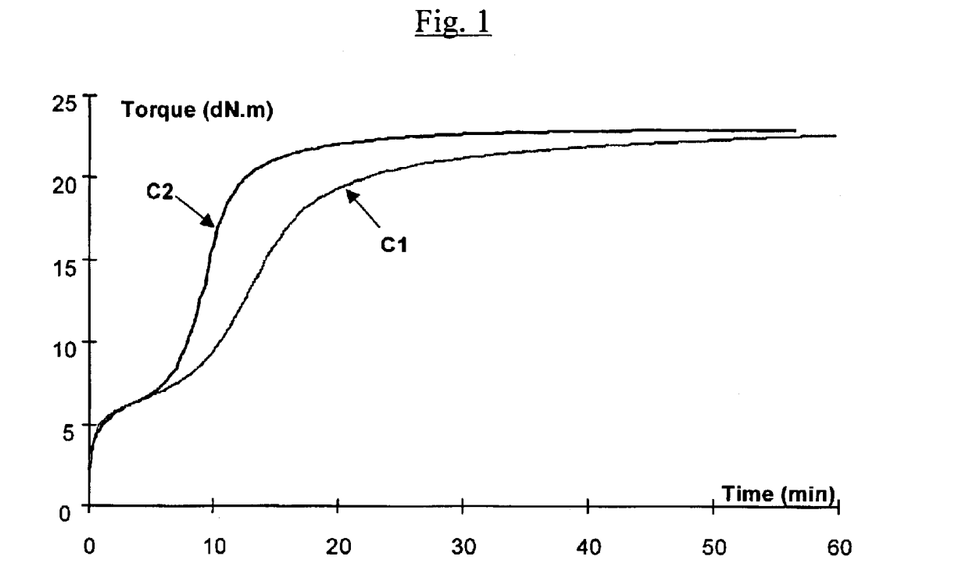
FIG. 1: rheograms (curing curves) recorded for rubber compositions comprising polyfunctional organosilanes, whether or not in accordance with the invention, as coupling agent.
Figure 2:
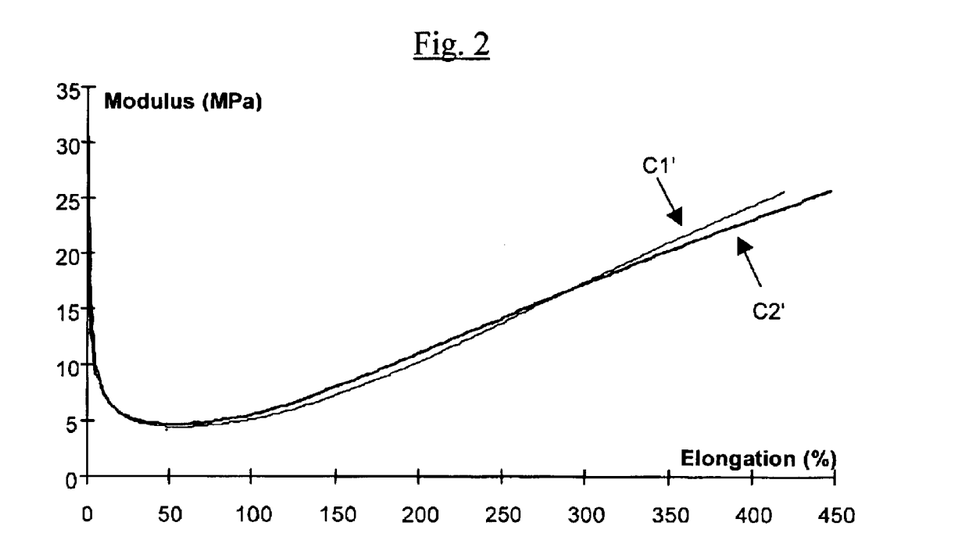
FIG. 2: curves of the variation of modulus as a function of elongation for these rubber compositions.

The attached FIGS. 1 and 2 respectively reproduce the rheograms (torque in dN.m as a function of duration of vulcanization in min) and modulus curves (in MPa) as a function of elongation (in %); these curves are denoted C1 and C2 on FIG. 1, then C1' and C2' on FIG. 2 and correspond respectively to compositions C-1 and C-2.

Examination of the various results of Table 2 gives rise to the following observations:
- the composition C-2 comprising product D exhibits a shorter scorching time than that of the control composition C-1, but this time T5 is sufficient to provide a satisfactory safety margin with regard to the problem of scorching;
- the Mooney plasticity values remain low (85 to 90 MU) in all cases, the lowest value moreover being recorded on composition C-2; this is indicative of very good processability of the rubber compositions in the uncured state, which is at least as good as that of conventional compositions using alkoxysilane polysulfides;
- after curing, composition C-2, in comparison with the control composition, exhibits modulus values at high deformation (M100 and M300) and an (M300/M100) ratio which are very close, these both being clear indicators to the person skilled in the art of the quality of coupling provided by product D;
- hysteresis properties seem slightly improved for the composition C-2, as illustrated by a lower $tan(\delta)_{max}$ value (synonymous with low rolling resistance);
- finally and above all, it will be noted that composition C-2 is unexpectedly distinguished by a conversion rate constant K which is more than twice as high as that of the control composition; in other words, curing of the composition may be performed in a distinctly shorter time.

The rheograms of the attached FIG. 1 confirm the superiority of composition C-2 containing the hydroxysilane of the invention: induction time approaching that of the control composition; maximum torque identical to that of the control composition, but achieved in a distinctly shorter time; higher conversion rate constant K.

FIG. 2 also confirms the preceding observations: curve C2' (composition C-2) and curve C1' (control composition C-1) are largely coincide, in particular for the greater elongations which are representative of the reinforcement and thus of the wear resistance capabilities of the rubber.

In summary, the overall behaviour of composition containing the monohydroxysilane of the invention not only reflects a high quality bond (or coupling) between the reinforcing inorganic filler and the diene elastomer, which is at least equal to that available with conventional alkoxysilane polysulfides such as TESPT, but also, unexpectedly, very distinctly improved vulcanizability.

Replacing a polysulfurised alkoxysilane such as TESPT with the polysulfurised hydroxysilane of the invention also constitutes a considerable advantage with regard to the environment and the problem caused by emissions of VOC ("volatile organic compounds"), since the alkoxyl groups of an alkoxysilane (such as the ethoxyl groups of TESPT) are in fact the cause of alcohol (ethanol) emissions, both during manufacture of the rubber compositions themselves and during curing of rubber articles incorporating these compositions.

In summary, the monohydroxysilane of the invention may thus particularly advantageously be used as a coupling agent in rubber compositions usable for the manufacture of tires, in particular treads for tires which have both low rolling resistance and high wear resistance, in particular when these treads are intended for tires for passenger vehicles or for industrial is vehicles of the heavy-vehicle type.

TABLE 1

|  | Composition No. | |
| --- | --- | --- |
|  | C-1 | C-2 |
| SBR (1) | 75 | 75 |
| BR (2) | 25 | 25 |
| silica (3) | 80 | 80 |
| alkoxysilane (4) | 6.4 | — |
| product D (5) | — | 4.6 |
| DPG (6) | 1.5 | 1.5 |
| ZnO | 2.5 | 2.5 |
| stearic acid | 2 | 2 |
| antioxidant (7) | 1.9 | 1.9 |
| sulfur | 1.1 | 1.1 |
| accelerator(8) | 2 | 2 |

(1) SBR with 59.5% of 1,2-polybutadiene units; 26.5% of styrene; extended with 37.5% by weight of aromatic oil (or 37.5 phr of oil per 100 phr of dry SBR); Tg = −29° C.; expressed in dry SBR;
(2) BR with 4.3% of 1,2; 2.7% of trans; 93% of cis-1,4 (Tg = −106° C.);
(3) silica type "HD" - "Zeosil 1165 MP" from Rhodia in the form of microbeads (BET and CTAB: approximately 150–160 m²/g);
(4) TESPT ("Si69" from DEGUSSA-HÜLS);
(5) product D synthesised (bis-(propyldimethylsilanol) polysulfide, 95 mol %);
(6) diphenylguanidine ("Vulcacit D" from Bayer);
(7) N-1,3-dimethylbutyl-N-phenyl-para-phenylenediamine ("Santoflex 6-PPD" from Flexsys);
(8) N-cyclohexyl-2-benzothiazyl sulfenamide ("Santocure CBS" from Flexsys).

TABLE 2

|  | Composition No. | |
| --- | --- | --- |
|  | C-1 | C-2 |
| Properties before curing: | | |
| ML1 + 4 (MU) | 90 | 85 |
| T5 (min) | 20 | 13 |
| $t_i$ (min) | 9 | 7 |
| $t_{99}$ (min) | 41 | 21 |
| K (min$^{-1}$) | 0.14 | 0.32 |
| $t_{99}-t_i$ (min) | 32 | 14 |
| Δ torque | 17.8 | 19.6 |
| Properties after curing: | | |
| M10 (MPa) | 7.0 | 6.8 |
| M100 (MPa) | 2.6 | 2.8 |
| M300 (MPa) | 4.4 | 4.3 |
| M300/M100 | 1.7 | 1.6 |
| tan (δ) max | 0.310 | 0.299 |
| Breaking stress (MPa) | 20.6 | 20.8 |
| Elongation at break (%) | 416 | 443 |

What is claimed is:

1. A monohydroxysilane polysulfide of the formula (I):

wherein the radicals R, identical or different, are hydrocarbon groups; radicals R', identical or different, are divalent linking groups; x is equal to or greater than 2.

2. The polysulfide according to claim 1, wherein the radicals R comprise from 1 to 15 carbon atoms and the radicals R' comprise from 1 to 18 carbon atoms.

3. The polysulfide according to claim 2, wherein the radicals R are selected from among $C_1$–$C_6$ alkyls, $C_5$–$C_8$ cycloalkyls and the phenyl radical, and wherein the radicals R' are selected from among $C_1$–$C_{18}$ alkylenes and $C_6$–$C_{12}$ arylenes.

4. The polysulfide according to claim 3, wherein the radicals R are selected from among $C_1$–$C_3$ alkyls and the radicals R' are selected from among $C_1$–$C_4$ alkylenes.

5. The polysulfide according to claim 4 having as formula (Me=methyl):

in which the radicals R' are $C_1$–$C_4$ alkylenes.

6. The polysulfide according to claim 5, wherein the radicals R' are selected from among methylene, ethylene and propylene.

7. The polysulfide according to claim 6, consisting of a bis-(propyidimethylsilanol) polysulfide of the formula:

8. The polysulfide according to claim 1, wherein x is within a range from 2 to 9.

9. The polysulfide according to claim 5 wherein x is within a range from 2 to 9.

10. The polysulfide according to claim 7 wherein x is within a range from 2 to 9.

11. The polysulfide according to claim 10, wherein the polysulfide is selected from among disulfides (x=2), trisulfides (x=3), tetrasulfides (x=4), pentasulfides (x=5), hexasulfides (x=6) and mixtures thereof.

12. The polysulfide according to claim 11, wherein x lies within a range from 2 to 4.

13. A process for obtaining a polysulfide according to claim 1, wherein said process comprises the following steps:

the starting compound is a halogenated organosilane (hereafter product A) of the formula (A) (Hal= halogen):

said organosilane is optionally subjected to alcoholysis under the action of an alcohol (R"—OH) in the presence of an organic base intended to scavenge the resultant acid halide, in order to obtain a monoalkoxysilane (hereafter product B) of the formula (B):

hydrolysis by the action of a hydroxyl donor is performed in an inert organic solvent:
either on the product (A) in the presence, in this case, of an organic base to scavenge the resultant acid halide, the hydroxyl donor being water;
or, if applicable, on the product (B), the hydroxyl donor being a inorganic base and the organic solvent a polar solvent, in order to obtain a monohydroxysilane (product C) of the formula (C):

finally, a sulfuration stage is performed on the product C by the action of a polysulfide to give rise to the intended product of the formula (I).

14. The process according to claim 13, wherein Hal is chlorine.

15. The process according to claim 13, wherein R" is selected from among $C_1$–$C_6$ alkyls.

16. The process according to claim 15, wherein R" is selected from among $C_1$–$C_3$ alkyls.

17. The process according to claim 13, wherein alcoholysis is performed at a temperature of less than 15° C.

18. The process according to claim 13, wherein the organic base intended to scavenge the acid halide which is formed, is a tertiary amine.

19. The process according to claim 13, wherein hydrolysis is performed directly on product A.

20. The process according to claim 13, wherein hydrolysis is performed on product B.

21. The process according to claim 20, wherein the polar organic solvent is selected from among $C_1$–$C_6$ alcohols.

22. The process according to claim 21, wherein the polar organic solvent is selected from $C_1$–$C_3$ alcohols.

23. The process according to claim 13, wherein the hydroxyl donor is used in excess relative to the quantity of product A or B.

24. The process according to claim 13, wherein the polysulfide of the sulfuration stage is an ammonium or metal polysulfide ($x \geq 2$), of the formula $M_2S_x$ or $M'S_x$ (M=alkali metal or $NH_4$; M'=Zn or alkaline-earth metal).

25. The process according to claim 24, wherein the polysulfide of the sulfuration stage is a sodium polysulfide $Na_2S_x$.

26. The process according to claim 25, wherein said polysulfide $Na_2S_x$ is obtained by the action of sulfur on $Na_2S$.

27. The process according to claim 24, wherein the sulfuration stage is performed in an aqueous phase.

28. The process according to claim 27, wherein the sulfuration stage is performed in a biphasic water/organic solvent medium.

29. The process according to claim 27 or 28, wherein the sulfuration stage is performed in the presence of a phase-transfer catalyst.

30. The process according to claim 29, wherein the sulfuration stage is performed in the presence of a salt of the formula M"Hal or M"$_2SO_4$, wherein M" is selected from among Li, Na and K; and Hal is selected from among F, Cl and Br).

* * * * *